(12) United States Patent
Hadley et al.

(10) Patent No.: US 10,149,775 B2
(45) Date of Patent: Dec. 11, 2018

(54) BARBED ANCHORS FOR ATTACHMENT TO ENDOLUMINAL PROSTHESIS

(71) Applicant: Cook Medical Technologies LLC, Bloomington, IN (US)

(72) Inventors: Rick Hadley, Otterbein, IN (US); William J. Havel, West Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 4 days.

(21) Appl. No.: 15/593,665

(22) Filed: May 12, 2017

(65) Prior Publication Data

US 2017/0246015 A1    Aug. 31, 2017

Related U.S. Application Data

(62) Division of application No. 13/951,926, filed on Jul. 26, 2013, now Pat. No. 9,681,965.

(60) Provisional application No. 61/677,689, filed on Jul. 31, 2012.

(51) Int. Cl.
*A61F 2/06*  (2013.01)
*A61F 2/848*  (2013.01)
*A61F 2/91*  (2013.01)

(52) U.S. Cl.
CPC .............. *A61F 2/848* (2013.01); *A61F 2/91* (2013.01); *A61F 2002/8483* (2013.01); *A61F 2220/0016* (2013.01)

(58) Field of Classification Search
CPC ............ A61B 17/0401; A61B 17/0469; A61B 17/0487; A61B 2017/045; A61B 2017/0456; A61B 17/12118; A61B 2017/0437; A61F 2/07; A61F 2/95; A61F 2/91; A61F 2002/075; A61F 2/848; A61F 2220/0016; A61F 2002/8483
See application file for complete search history.

(56) References Cited

U.S. PATENT DOCUMENTS

| 4,759,758 | A | 7/1988 | Gabbay |
| 6,231,581 | B1 * | 5/2001 | Shank ............... A61B 17/064 606/157 |
| 7,572,289 | B2 | 8/2009 | Sisken et al. |
| 8,029,518 | B2 | 10/2011 | Goldfarb et al. |

(Continued)

FOREIGN PATENT DOCUMENTS

| EP | 2 481 381 A1 | 8/2012 |
| WO | 2010/024881 A1 | 3/2010 |
| WO | 2013/040373 A1 | 3/2013 |

OTHER PUBLICATIONS

Examination Report Issued in European application No. 13 275 174.4, dated Jun. 11, 2015 (7 pgs).

(Continued)

*Primary Examiner* — Ann Schillinger
(74) *Attorney, Agent, or Firm* — Brinks Gilson & Lione

(57) ABSTRACT

An endoluminal prosthesis that includes a support structure having a plurality of struts and an anchor that is attachable to the support structure. The anchor includes an anchor body and one or more barbs extending outwardly from the anchor body. The anchor body includes a cannula having a first end, a second end, and a middle section. The middle section includes a plurality of open portions arranged in a plurality of arrays around the anchor body.

18 Claims, 3 Drawing Sheets

(56) References Cited

U.S. PATENT DOCUMENTS

| | | | |
|---|---|---|---|
| 8,696,739 B2* | 4/2014 | Dierking | A61F 2/848 623/1.15 |
| 2003/0120331 A1 | 6/2003 | Chobotov et al. | |
| 2005/0038497 A1 | 2/2005 | Neuendorf et al. | |
| 2005/0240259 A1 | 10/2005 | Sisken et al. | |
| 2009/0048664 A1 | 2/2009 | Cage | |
| 2010/0016953 A1 | 1/2010 | Sisken et al. | |
| 2010/0057195 A1 | 3/2010 | Roeder et al. | |
| 2011/0008405 A1* | 1/2011 | Birdsall | A61L 31/022 424/423 |

OTHER PUBLICATIONS

Search Report issued in European application No. 13 275 174.4, dated Nov. 12, 2013 (7 pgs).
Response to Examination Report issued in European application No. 13 275 174.4, dated Sep. 28, 2015 (16 pgs).
Notice of Acceptance from EPO dated Nov. 23, 2015 (40 pgs).

* cited by examiner

BARBED ANCHORS FOR ATTACHMENT TO ENDOLUMINAL PROSTHESIS

RELATED APPLICATIONS

The present patent document is a divisional of and claims priority to U.S. patent application Ser. No. 13/951,926, filed on Jul. 26, 2013, which claims the benefit of the filing date under 35 U.S.C. § 119(e) of U.S. Provisional Patent Application Ser. No. 61/677,689, filed Jul. 31, 2012, which are hereby incorporated by reference in their entirety.

TECHNICAL FILED

Attachable anchors including barbs to a stent and methods for attaching the anchor to the stents are disclosed here.

BACKGROUND

Barbs attached to prosthetic devices including stents, vena cava filters, valves, and other intraluminal devices for treatment of aortic aneurisms and other related vascular diseases help to secure placement of the prosthesis after implantation and deployment in the treated vessel or other conduit. The barbs are positioned to engage and embed into the walls of the treated vessel for permanent attachment. Some barb designs present limitations to barb placement and the life of the barb depending on the design of the stent. High stress or stain near regions on a wire stent caused by limitations of the barb design and the method of attachment of the barb to the wire stent may result in fatigue and failure of the stent and barb fatigue or fracture.

There remains a continuing need for a barb design and method for attachment thereof that reduces barb failure after implantation of the device. A barb design that reduces the likelihood of failure eliminates the need for any additional surgical procedures if the device becomes displaced after barb failure and any patient discomfort and potential risks involved in additional procedures and device displacement. Accordingly, embodiments of a new barb design and methods of attachment to a prosthetic device that substantially reduce barb failure or fracture have been developed.

BRIEF SUMMARY

Embodiments disclosed here may include an endoluminal prosthesis. The prosthesis may include a support structure, such as a stent, having a plurality of struts and an anchor that is attachable to the support structure. The anchor includes an anchor body and one or more barbs extending outwardly from the anchor body. The anchor body includes a cannula having a first end, a second end, and a middle section. The middle section includes a plurality of open portions arranged in a plurality of arrays around the anchor body.

In further embodiments, the plurality of open portions include a first end, a second end and a middle portion. The middle portion includes a linear shape, and the first and second ends include a circular shape. The circular shape of each first end and each second end of the open portions provide relief to reduce stress concentrations at the ends of the linear shape of the middle section.

Additional embodiments may include a plurality of bands arranged around the anchor body for attaching the anchor body to one of the plurality of struts of the support structure. The plurality of bands and the plurality of arrays of open portions may be positioned in an alternating pattern along the anchor body. The plurality of bands provide multiple rings of contact for affixing the anchor to the support structure. The multiple rings of contact along with the plurality of open portions reduce any friction created when positioning the anchor on the support structure that may cause fatigue or failure and reduce stress concentrations on the support structure after positioning.

Another embodiment may include a method for attaching an anchor to an endoluminal support structure having a plurality of struts. The method of attaching includes providing an anchor including an anchor body and a plurality of barbs extending outwardly from the anchor body, the anchor body including a cannula having a plurality of open portions arranged in a plurality of arrays around the anchor body, and a plurality of bands arranged around the anchor body and between each array of relief segments. The method of attaching further includes positioning the cannula over a strut of the endoluminal support structure and affixing the cannula to the support structure at the plurality of bands.

DETAILED DESCRIPTION

Figure 1:
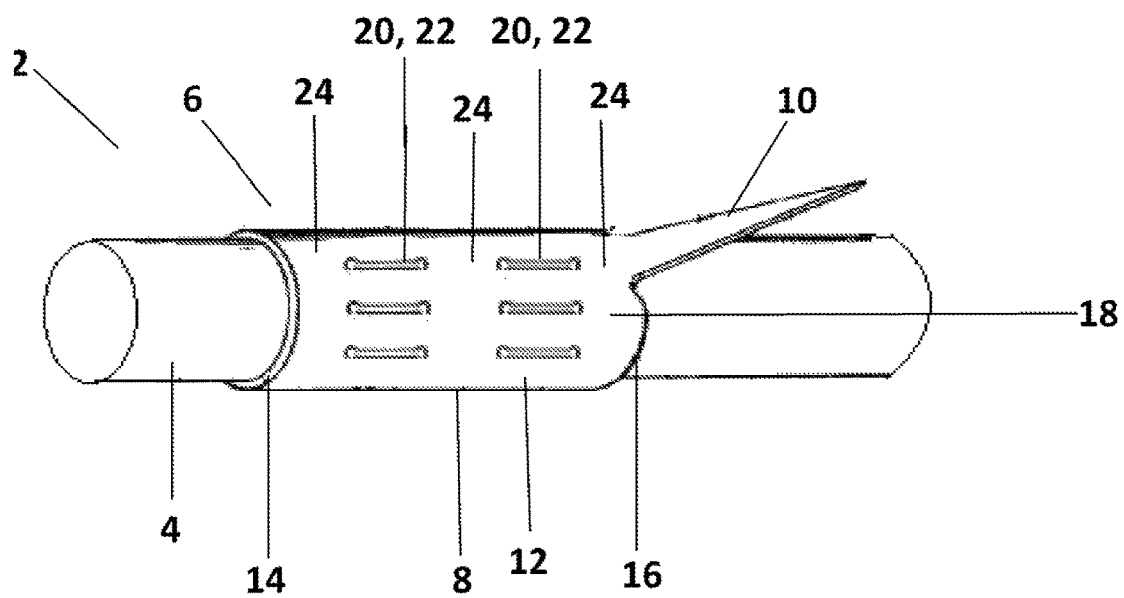
FIG. 1 shows a perspective view of the endoluminal prosthesis including a support structure and an anchor.

The term "prosthesis" means any replacement for a body part or for a function of that body part or any device that enhances or adds functionality to a physiological system.

The term "support structure" means any device that is attached to a prosthesis. For example, a support structure can comprise stents, radiopaque markers, anchoring stents, barbs, and lateral support rings for supporting an open portion. The structural components can be attached to the exterior of the graft, the interior of the graft, and/or can be sandwiched between two or more layers of graft material.

The support structure can be made from numerous base materials, such as: biocompatible metals or other metallic materials; polymers including bioabsorbable or biostable polymers; stainless steels; nickel-titanium alloys including shape memory or superelastic types (e.g., nitinol or elastinite); noble metals including platinum, gold, or palladium; refractory metals including tantalum, tungsten, molybdenum, or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold, and/or tantalum alloys); iron-based alloys (e.g., including platinum, gold, and/or tantalum alloys); cobalt-based alloys (e.g., including platinum, gold, and/or tantalum alloys); cobalt-chrome alloys (e.g., elgiloy); cobalt-chromium-nickel alloys (e.g., phynox); alloys of cobalt, nickel, chromium, and molybdenum; cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate); composites; any mixture, blend, alloy, copolymer or combination of any of these; or various other suitable materials not limited by these examples.

The term "stent" means any device that provides rigidity, expansion force, or support to a prosthesis, such as a stent graft. In one configuration, the stent can represent a plurality of discontinuous devices. In another configuration, the stent can represent one device. Stents can have a wide variety of configurations and can be balloon-expandable or self-expanding. Typically, stents have a circular cross-section when fully expanded, so as to conform to the generally circular cross-section of a body lumen. In one example, a stent can comprise struts (elongate portions) and acute bends (curvilinear portions) that are arranged in a zig-zag configuration, as exemplified in a Z-stent, in which the struts are set at angles to each other and are connected by the acute bends.

The terms "swage fitted," "swage fitting," "swage fit," or "swaging" means any process that provides a means for attaching any device to a support structure including shaping, molding, forming, forging, bending, squeezing, working, or hammering the device to achieve a particular shape. The process may include cooling or heating the device to facilitate the process.

A variety of biocompatible materials can be employed to construct the stent, or portions of the stent, including metals and/or alloys, medically-acceptable polymers and/or bioabsorbable polymers, or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In a preferred configuration, the stent is constructed from nitinol, stainless steel, and/or cobalt-chromium alloys.

Figure 2:
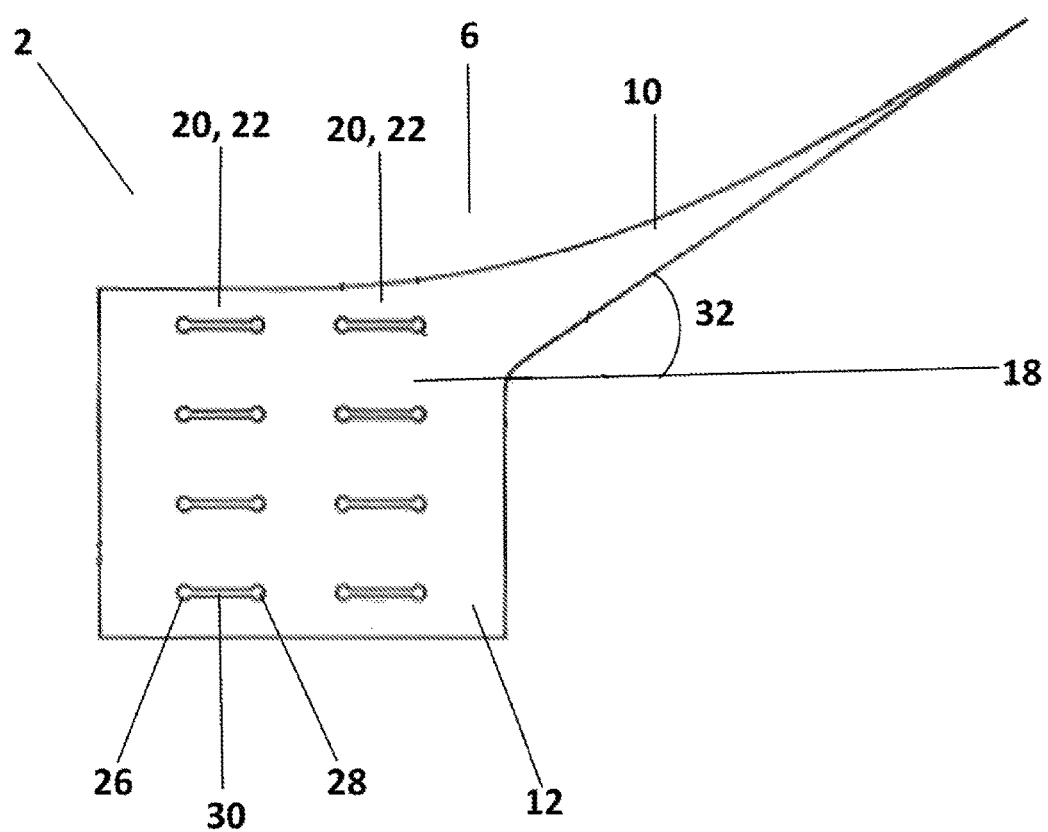
FIG. 2 shows a side view of the anchor of FIG. 1.
Figure 3:
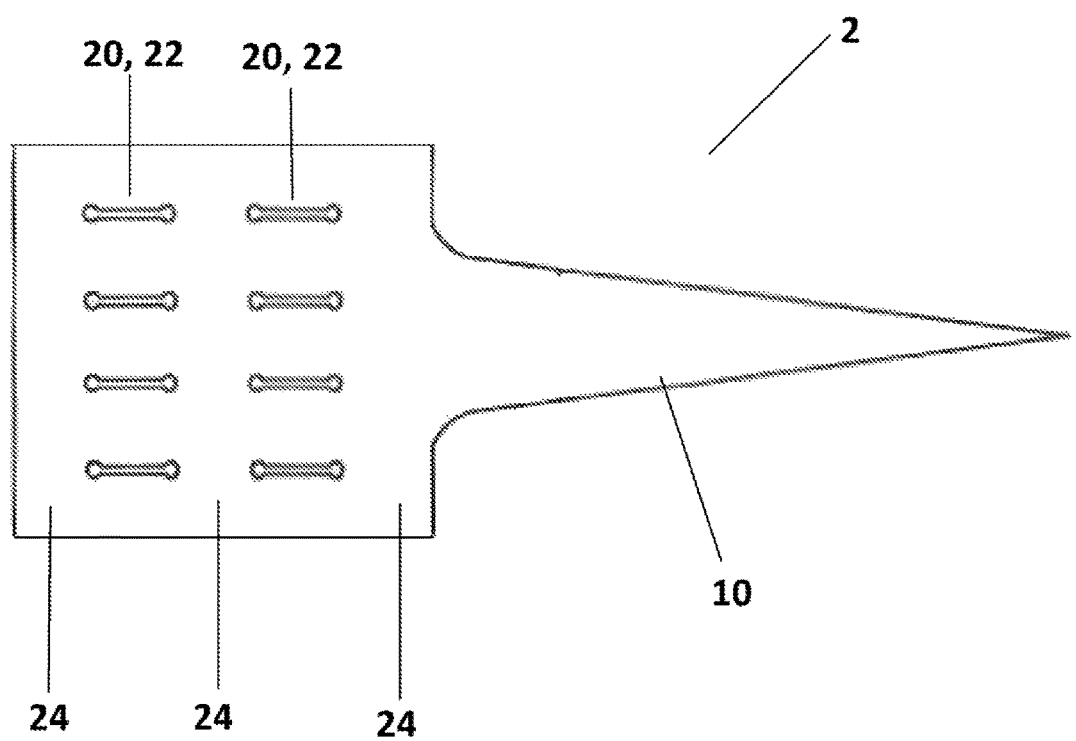
FIG. 3 shows a top view of the anchor of FIG. 1.

Embodiments are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments of the present invention, such as—for example—conventional fabrication and assembly. The terms "distal" and "proximal" are to be understood with their standard usages, referring to the direction away from and the direction toward the handle/user end of a tool or device, respectively (i.e., the term "distal" means the direction or portion of the device that is farthest from the plurality of barbs and the term "proximal" means the portion of the device that is nearest to the plurality of barbs). In FIGS. 1-3 of this application, first corresponds with distal and second corresponds with proximal.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

FIGS. 1-3 depict an embodiment of an endoluminal prosthesis 2 that includes a support structure 4 and an anchor or anchoring device 6. The support structure 4 includes a plurality of struts. The anchor 6 includes an anchor or main body 8 and one or more barbs 10 for securing placement of the prosthesis 2 after implantation and deployment in the treated vessel by embedding into the walls of the treated vessel. The anchor 6 may be formed in one piece and be stamped, machined, or laser cut out of a sheet of biocompatible material.

The anchor body 8 illustrated in FIGS. 1-3 is laser cut, machined or otherwise formed out of a piece of cannula 12. The cannula 12 has a first or distal end 14, a second or proximal end 16, and a middle section or longitudinal axis 18. The middle section 18 includes a plurality of open portions 20 that are arranged in a plurality of arrays 22 around the anchor body 8. The middle section 18 may also include a plurality of bands or ring bands 24 for attaching the anchor body 8 to one of the plurality of struts and are arranged around the anchor body 8. The plurality of arrays 22 of open portions 20 and the plurality of bands 24 are arranged in an alternating pattern along the anchor body 8. The preferred size and material of the cannula 12 may be determined by the dimensions of the strut to which the anchor body 8 is attached.

Referring to FIG. 1, the anchor body 8 may be attached to the support structure 4 at the plurality of bands 24 by swage fit or other fastening means. The anchor 6 may slide onto a strut of the support structure 4 and placed into a preferred position on the strut. A swag fitting tool or a mechanical tool may be used to reduce the diameter of the anchor 6 at the plurality of bands 24 for attachment of the anchor 6 to the support structure 4. The plurality of bands 24 provide multiple contact regions for attachment permitting greater affixation of the anchor 6 to the support structure 4. The preferred size of the anchor body 8 may be determined by the dimensions of the strut to which the anchor body 8 is attached. The anchor body 8 may have geometries permitting the anchor 6 to slide onto the strut of the support structure 4 with minimal difficulty or friction and be swage fitted to the support structure 4.

FIG. 2 depicts a side view of the endoluminal prosthesis 2. The open portions 20 shown in FIG. 2 include a first end 26, a second end 28, and a middle section 30. The first end 26 and the second end 28 include a circular shape. The middle section 30 includes a linear shape. The open portions 20 can be formed by laser cutting on the cannula 12. The circular shape of each first end 26 and each second end 28 of the open portions 20 provide relief to reduce stress concentrations at the ends of the linear shape of the middle section 30. The open portions 20 also provide relief to reduce stress concentrations on the support structure 4 when the anchor 6 is affixed to the support structure 4 along the plurality of bands 24. The pattern of the open portions 20 and the multiple contact regions provided by the plurality of bands 24 along the anchor body 8 simplify the positioning and fit of the anchor 6 on the support structure 4 by reducing any friction created when sliding the anchor 6 along the support structure 4 for placement.

The anchor 6 also includes one or more barbs 10 to secure the endoluminal prosthesis 2 to the wall of the treated vessel. The barb 10 depicted in FIG. 2 may extend outwardly from the anchor body 8. The barb 10 may be set at an angle 32 from the longitudinal axis 18 of the cannula 12.

FIG. 3 depicts a top view of the endoluminal prosthesis 2. FIG. 3 depicts one embodiment of the endoluminal prosthesis 2 wherein the plurality of arrays 22 includes two arrays 22 of open portions 20 and the plurality of bands 24 includes three bands 24.

A method of attaching the anchor 6 to the support structure 4 includes positioning the cannula 12 over a strut of the plurality of struts of the support structure 4 to a desired location. The anchor 6 may be attached or affixed to the support structure 4 at the plurality of bands 24. The cannula 12 of the anchor 6 may be affixed to the strut by swage fit or other fastening means by use of a swag fitting tool or other mechanical tool.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

The invention claimed is:

1. A method of attaching an anchor to an endoluminal support structure comprising at least one strut, the method comprising:
    presenting an anchor comprising an anchor body and one or more barbs extending outwardly from the anchor body, wherein the anchor body comprises a cannula comprising at least one open portion arranged in at least two arrays around the anchor body and a plurality of bands arranged around the anchor body, wherein the at least one open portion comprises a perimeter that encloses the at least one open portion, the perimeter having a length parallel to a longitudinal axis of the cannula and a width perpendicular to the longitudinal axis, wherein the length of the at least one open portion is greater than the width, and wherein the at least one open portion further comprises a first end, a second end, and a middle section, the first end comprising a circular shape, the second end comprising a circular shape, and the middle section comprising a linear shape;
    positioning the anchor body over the at least one strut of the endoluminal support structure; and
    affixing the anchor body to the at least one strut of the endoluminal support structure at the plurality of bands.

2. The method of claim 1, wherein the at least one open portion comprises three open portions.

3. The method of claim 1, wherein the at least one open portion is configured to provide stress relief and release.

4. The method of claim 1, wherein the affixing of the anchor body to the at least one strut comprises swage fitting.

5. The method of claim 1, wherein the affixing of the anchor body to the at least one strut at the plurality of bands reduces a diameter of the cannula of the anchor body at the plurality of bands.

6. The method of claim 1, wherein the positioning of the anchor body to the at least one strut of the endoluminal support structure comprises sliding the anchor onto the at least one strut of the endoluminal support structure to a desired location.

7. The method of claim 1, wherein the at least two arrays and the plurality of bands are positioned in an alternating pattern along the anchor body.

8. The method of claim 7, wherein the alternating pattern along the anchor body of the at least two arrays and the plurality of bands reduces friction during the positioning of the anchor body over the at least one strut of the endoluminal support structure.

9. A method of attaching an anchor to an endoluminal support structure, the method comprising:
    presenting an anchor comprising an anchor body, wherein the anchor body comprises a cannula comprising a plurality of open portions arranged in at least two arrays around the anchor body and a plurality of bands arranged around the anchor body, and wherein each of the plurality of open portions comprises a perimeter that encloses each of the plurality of open portions, the perimeter having a length parallel to a longitudinal axis of the anchor body and a width perpendicular to the longitudinal axis, wherein the length of each of the plurality of open portions is greater than the width, and wherein each of the plurality of open portions further comprises a first end, a second end, and a middle section, the first end comprising a circular shape, the second end comprising a circular shape, and the middle section comprising a linear shape;
    positioning the anchor over the endoluminal support structure; and
    affixing the anchor to the endoluminal support structure at the plurality of bands.

10. The method of claim 9, wherein the plurality of open portions comprises at least three open portions.

11. The method of claim 9, wherein the plurality of open portions are configured to provide stress relief and release.

12. The method of claim 9, wherein the affixing of the anchor to the endoluminal support structure at the plurality of bands reduces a diameter of the anchor body at the plurality of bands.

13. The method of claim 9, wherein the at least two arrays and the plurality of bands are positioned in an alternating pattern along the anchor body.

14. The method of claim 13, wherein the alternating pattern along the anchor body of the at least two arrays and the plurality of bands reduces friction during the positioning of the anchor over the endoluminal support structure.

15. The method of claim 9, wherein the affixing of the anchor to the endoluminal support structure at the plurality of bands comprises swage fitting.

16. A method of manufacturing an anchor for an endoluminal prosthesis, the method comprising:
    presenting the anchor comprising an anchor body and one or more barbs extending outwardly from the anchor body, wherein the anchor body comprises a cannula; and
    laser cutting a plurality of open portions arranged in at least two arrays around the anchor body;
    wherein the laser cutting of the plurality of open portions comprises laser cutting a perimeter that encloses each of the plurality of open portions, the perimeter having a length parallel to a longitudinal axis of the cannula and a width perpendicular to the longitudinal axis, wherein the length is greater than the width; and
    wherein the laser cutting of the plurality of open portions also comprises laser cutting within the perimeter of each of the plurality of open portions a first end, a second end, and a middle section, the first end comprising a circular shape, the second end comprising a circular shape, and the middle section comprising a linear shape.

17. The method of claim 16, wherein the plurality of open portions comprises at least three open portions.

18. The method of claim 16, wherein the plurality of open portions are configured to provide stress relief and release.

* * * * *